United States Patent
Kimchy et al.

(10) Patent No.: US 10,098,599 B2
(45) Date of Patent: Oct. 16, 2018

(54) NANO PARTICLE DETECTION WITH X-RAY CAPSULE

(71) Applicant: CHECK-CAP LTD., Isfiya (IL)

(72) Inventors: Yoav Kimchy, Haifa (IL); Shlomo Lewkowicz, Tivon (IL)

(73) Assignee: CHECK-CAP LTD., Isfiya (IL)

( * ) Notice: Subject to any disclaimer, the term of this patent is extended or adjusted under 35 U.S.C. 154(b) by 24 days.

(21) Appl. No.: 15/505,612

(22) PCT Filed: Oct. 12, 2015

(86) PCT No.: PCT/IL2015/051016
§ 371 (c)(1),
(2) Date: Feb. 22, 2017

(87) PCT Pub. No.: WO2016/059631
PCT Pub. Date: Apr. 21, 2016

(65) Prior Publication Data
US 2018/0214104 A1    Aug. 2, 2018

Related U.S. Application Data

(60) Provisional application No. 62/062,882, filed on Oct. 12, 2014.

(51) Int. Cl.
*G06K 9/00* (2006.01)
*A61B 6/00* (2006.01)
(Continued)

(52) U.S. Cl.
CPC .............. *A61B 6/50* (2013.01); *A61B 6/4057* (2013.01); *A61B 6/425* (2013.01); *A61B 6/4241* (2013.01);
(Continued)

(58) Field of Classification Search
CPC ..... A61B 6/4057; A61B 6/4241; A61B 6/425; A61B 6/485; A61B 6/50; A61K 49/0065;
(Continued)

(56) References Cited

U.S. PATENT DOCUMENTS

2004/0170561 A1* 9/2004 Salb ................... A61B 6/4035
424/9.4
2007/0161885 A1* 7/2007 Kimchy ................ A61B 5/073
600/407
(Continued)

*Primary Examiner* — Amara Abdi
(74) *Attorney, Agent, or Firm* — Soroker Agmon Nordman

(57) ABSTRACT

A colon imaging system, including an imaging capsule, having: a. a radiation source providing X-Ray and gamma radiation with energies sufficient to induce X-Ray fluorescence from nanoparticles that adhere to cancerous tissue, and which were administered to a patient in a solution prior to examining the colon with the imaging capsule; b. a detector for detecting particle energy of particles emitted responsive to the provided radiation and forming count information disclosing a number of particles detected for each energy level; c. a transceiver for transferring the count information to an external computer for analysis, and also having a computer for constructing images of an inside of the colon based on the count information; wherein the images provide an indication of locations in the colon of which the nanoparticles adhere to.

20 Claims, 4 Drawing Sheets

(51) Int. Cl.
*A61K 49/00* (2006.01)
*G01N 23/223* (2006.01)
*A61K 49/04* (2006.01)
*B82Y 15/00* (2011.01)

(52) U.S. Cl.
CPC .......... *A61B 6/485* (2013.01); *A61K 49/0065* (2013.01); *A61K 49/0428* (2013.01); *G01N 23/223* (2013.01); *B82Y 15/00* (2013.01)

(58) Field of Classification Search
CPC ... A61K 49/0428; G01N 23/223; B82Y 15/00
See application file for complete search history.

(56) References Cited

U.S. PATENT DOCUMENTS

| | | | |
|---|---|---|---|
| 2008/0207999 A1* | 8/2008 | Abraham-Fuchs | A61B 1/00158 600/118 |
| 2012/0244075 A1* | 9/2012 | Liu | A61K 41/0052 424/9.1 |
| 2014/0066762 A1* | 3/2014 | Hwu | A61K 49/0065 600/431 |
| 2015/0353580 A1* | 12/2015 | Hutchison | C07F 1/005 436/164 |

* cited by examiner

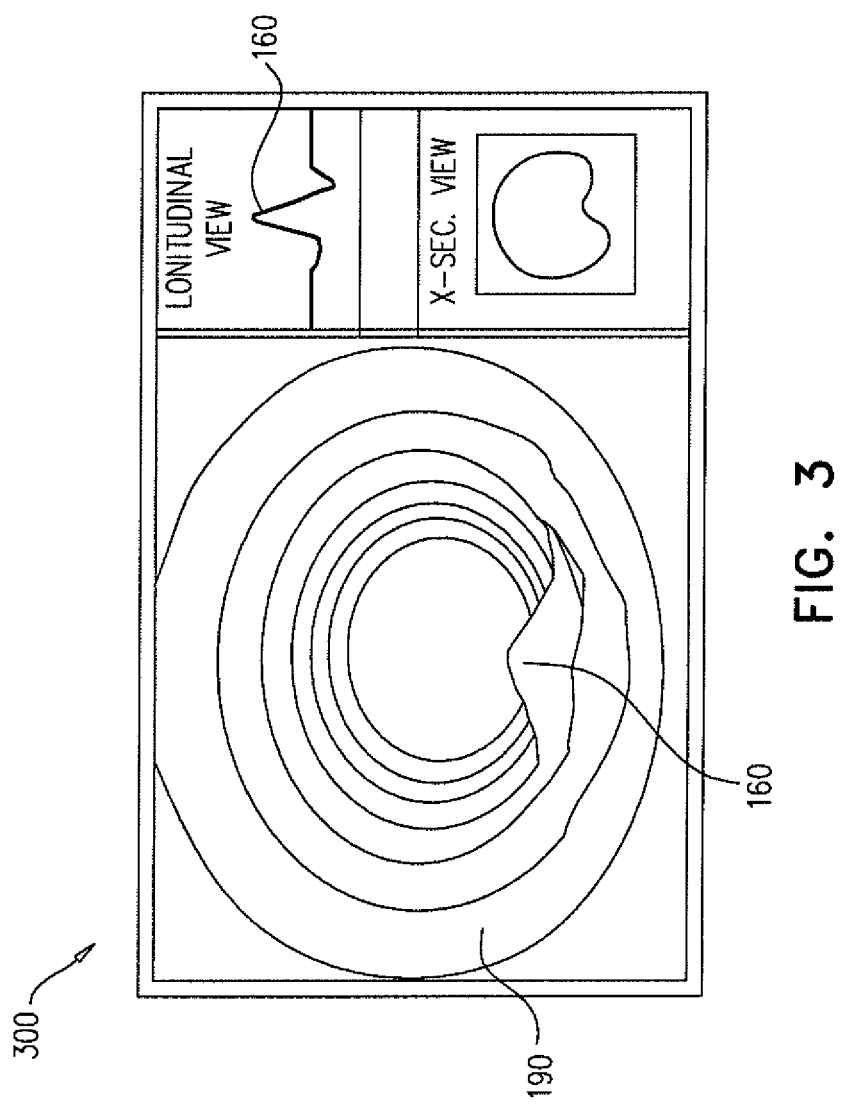

NANO PARTICLE DETECTION WITH X-RAY CAPSULE

RELATED APPLICATIONS

This application claims priority under 35 U.S.C. 120 from U.S. provisional application No. 62/062,882 dated Oct. 12, 2014, the disclosure of which is incorporated herein by reference.

FIELD OF THE DISCLOSURE

The present disclosure relates generally to the detection of pre-cancerous and cancer tissue in the colon using an X-Ray capsule and more specifically to enhancing detection by having the subject swallow a liquid solution with nanoparticles coated with molecules that are designed to latch onto cancerous tissue.

BACKGROUND OF THE DISCLOSURE

One method for examining the gastrointestinal tract for the existence of polyps and other clinically relevant features that may indicate regarding the potential of cancer is performed by swallowing an imaging capsule that travels through the gastrointestinal tract and views the patient's situation from within. In a typical case the trip can take between 24-48 hours after, which the imaging capsule exits in the patient's feces. Typically the patient swallows a contrast agent to enhance the imaging ability of the imaging capsule. Then the patient swallows the imaging capsule to examine the gastrointestinal tract while flowing through the contrast agent. The imaging capsule typically includes a radiation source, for example including a radioisotope that emits X-rays and/or Gamma rays. The radiation is typically collimated to allow it to be controllably directed toward a specific area during the imaging process. In an exemplary case the imaging capsule is designed to measure X-Ray fluorescence and/or Compton back-scattering and transmit the measurements (e.g. count rate, particle energy) to an external analysis device, for example a computer or other dedicated instruments.

U.S. Pat. No. 7,787,926 dated Aug. 31, 2010 and U.S. Pat. No. 9,037,219 dated May 19, 2015 both by the current applicant, the disclosures of which are incorporated herein by reference, describe details related to the manufacture and use of such an imaging capsule.

Alternatively, an X-Ray capsule attached to a tube may be introduced from the patient's anus to examine the colon. In either case the images need to be examined carefully by a trained expert to identify cancerous tissue, which may be easily overlooked. It is thus desirable to enhance the ability to locate cancerous tissue from the images provided by the X-ray capsule.

SUMMARY OF THE DISCLOSURE

An aspect of an embodiment of the disclosure, relates to a system and method for imaging a patient's colon to detect cancerous tissue. The method includes having the patient first swallow a solution with nanoparticles, for example gold nanoparticles, which are coated with a molecule that causes the nanoparticles to adhere to cancerous tissue in the colon. Optionally, the solution may also include a radio opaque contrast agent to enhance the imaging measurements. The user then swallows an imaging capsule to traverse the colon and identify locations having cancerous polyps/tumors based on the nanoparticles that latched themselves to those positions. Alternatively, the imaging capsule may be administered through the patient's anus directly into the colon with a colonoscopy tube.

As the imaging capsule traverses the colon it radiates the inner walls of the colon and uses detectors to measure the energy of particles returning to the imaging capsule in response to the emitted radiation. The detectors are configured to count the number of particles returned within specific ranges of energy levels, for example between 32-36 KeV, 49-57 Kev and 67-77 Kev. The count information represents the X-Ray fluorescence and Compton backscattering from the content of the colon (e.g. tissue and contrast agent) and from the nanoparticles adhering to cancerous tissue. The count information is transferred to a computer to be used to construct an image or images of the inner walls of the colon and especially the locations having nanoparticles adhering to them. The computer displays the images to a practitioner and may mark the locations having nanoparticles, for example with bright colors or a special pattern so that the practitioner will take notice of those locations. In some embodiments of the disclosure, the markings may vary dependent on the density of nanoparticles adhering to the location so that a level of severity may be determined (e.g. a high count resulting from a high density of nanoparticles).

There is thus provided according to an exemplary embodiment of the disclosure, a colon imaging system, comprising:

an imaging capsule, including:
  a. a radiation source providing X-Ray and gamma radiation with energies sufficient to induce X-Ray fluorescence from nanoparticles that adhere to cancerous tissue, and which were administered to a patient in a solution prior to examining the colon with the imaging capsule;
  b. a detector for detecting particle energy of particles emitted responsive to the provided radiation and forming count information disclosing a number of particles detected for each energy level;
  c. a transceiver for transferring the count information to an external computer for analysis;
a computer for constructing images of an inside of the colon based on the count information; wherein the images provide an indication of locations in the colon of which the nanoparticles adhere to.

In an exemplary embodiment of the disclosure, the nanoparticles are made from gold and coated with molecules that adhere to cancerous tissue. Optionally, the imaging capsule is designed to be administered by being swallowed by the patient. In an exemplary embodiment of the disclosure, the imaging capsule is connected to a tube for administering it through the anus of the patient. Optionally, the detector is configured to detect specific ranges of energy levels, forming a single count value for each range and ignoring particles with energies outside of the specific ranges. In an exemplary embodiment of the disclosure, the detected ranges include energy levels representing X-Ray fluorescence resulting from radiating the contents of the colon other than the nanoparticles. Optionally, the detected ranges include energy levels representing X-Ray fluorescence resulting from radiating the nanoparticles. In an exemplary embodiment of the disclosure, the detected ranges include energy levels representing Compton Backscattering resulting from radiating the contents of the colon. Optionally, the detected ranges include energy levels representing Compton Backscattering resulting from particles with energies that are higher than the energies of the X-Ray fluorescence particles.

In an exemplary embodiment of the disclosure, the locations of the nanoparticles are marked in the images by specific colors or patterns. Optionally, the markings in the images of the locations of the nanoparticles provide an indication of the density of nanoparticles at the location. In an exemplary embodiment of the disclosure, the image is formed as a combination of the anatomical shape of the colon with the physiological behavior of different tissue areas as an overlay.

There is further provided according to an exemplary embodiment of the disclosure, a method of detecting cancerous tissue in a colon, comprising:

swallowing a solution with nanoparticles that adhere to cancerous tissue;

introducing into the colon an imaging capsule to examine the colon;

radiating internal walls of the colon with a radiation source providing X-Ray and gamma radiation with energies sufficient to induce X-Ray fluorescence from the nanoparticles that adhere to cancerous tissue detecting particle energy of particles emitted responsive to the provided radiation and forming count information disclosing a number of particles detected for each energy level;

transferring the count information to an external computer for analysis;

constructing images of an inside of a colon based on the count information; wherein the images provide an indication of locations in the colon of which the nanoparticles adhere to.

In an exemplary embodiment of the disclosure, the nanoparticles are made from gold and coated with molecules that adhere to cancerous tissue. Optionally, the imaging capsule is designed to be administered by being swallowed by the patient. In an exemplary embodiment of the disclosure, the imaging capsule is connected to a tube for administering it through the anus of the patient. Optionally, the detector is configured to detect specific ranges of energy levels, forming a single count value for each range and ignoring particles with energies outside of the specific ranges. In an exemplary embodiment of the disclosure, the detected ranges include energy levels representing X-Ray fluorescence resulting from radiating the contents of the colon other than the nanoparticles. Optionally, the detected ranges include energy levels representing X-Ray fluorescence resulting from radiating the nanoparticles. In an exemplary embodiment of the disclosure, the locations of the nanoparticles are marked in the images by specific colors or patterns. In an exemplary embodiment of the disclosure, the markings in the images of the locations of the nanoparticles provide an indication of the density of nanoparticles at the location.

BRIEF DESCRIPTION OF THE DRAWINGS

The present disclosure will be understood and better appreciated from the following detailed description taken in conjunction with the drawings. Identical structures, elements or parts, which appear in more than one figure, are generally labeled with the same or similar number in all the figures in which they appear, wherein:

FIG. 3 is a schematic illustration of a snapshot of a computer display showing reconstructed images of a colon, according to an exemplary embodiment of the disclosure.

DETAILED DESCRIPTION

In an exemplary embodiment of the disclosure, a patient swallows a radio opaque contrast agent solution (e.g. based on Barium or Iodine) which mixes with the content of their gastrointestinal tract to increase the accuracy in detecting cancerous tissue based on the measurements taken from inside the patient's body. Optionally, the contrast agent solution includes a large amount of nanoparticles (e.g. millions or billions or more), which are designed to attach themselves especially to tumors/polyps/cancerous tissue cells and enhance the response to X-ray radiation and/or gamma radiation (e.g. increase an X-Ray fluorescence (XRF) count). Optionally, the nanoparticles are made from a metal, for example gold (Au 79) and coated at least on one side with a molecule that is attracted to cancerous cells, for example the nanoparticles may be coated with peptides or larger proteins that are designed to recognize targets on early cancer cells. In some embodiments of the disclosure, the nanoparticles are administered independently in a separate solution. During an imaging process the nanoparticles will enhance the response from the cancerous cells to prevent them from being overlooked.

Figure 1A:
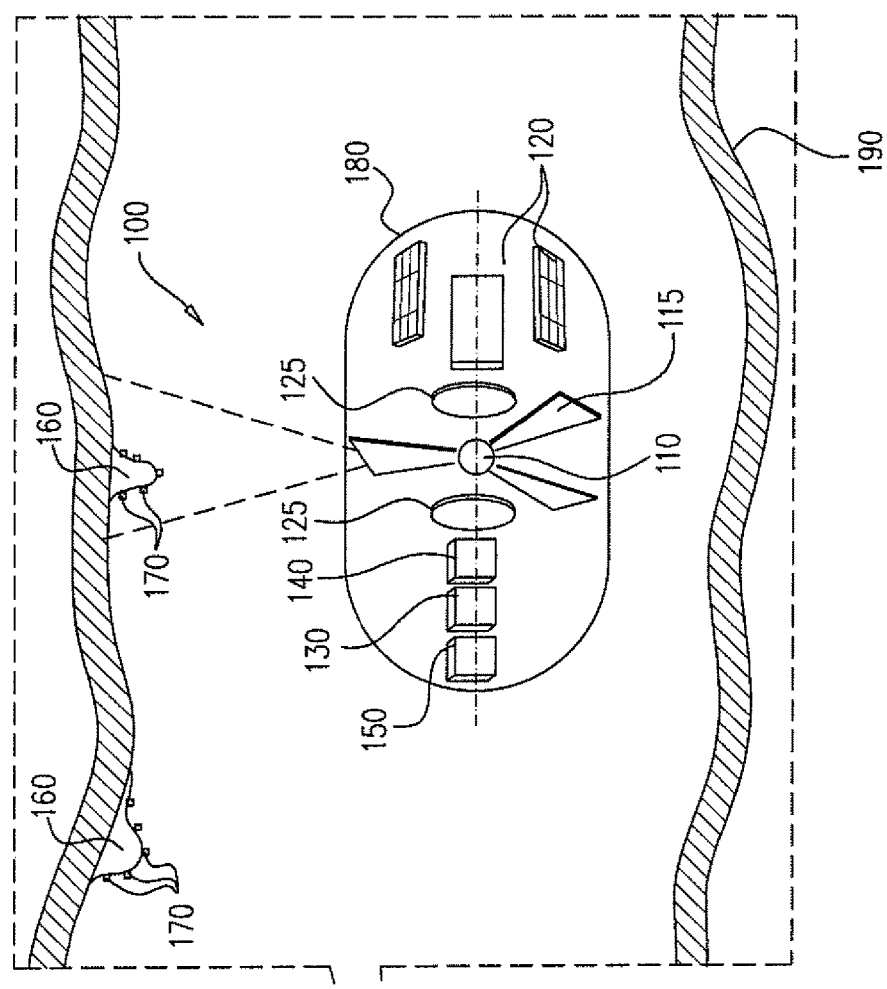
FIG. 1A is a schematic illustration of a perspective view of an imaging capsule in a patient's colon, according to an exemplary embodiment of the disclosure.
Figure 1A:
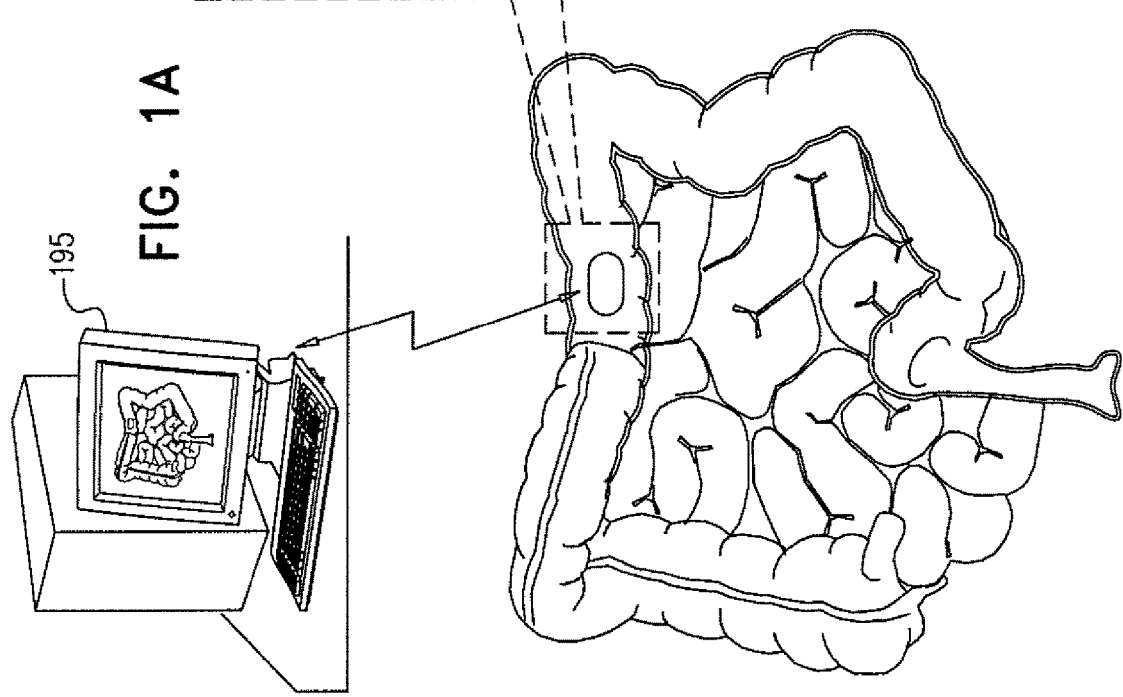

FIG. 1A is a schematic illustration of a perspective view of an imaging capsule 100 in a patient's colon 190, according to an exemplary embodiment of the disclosure.

Optionally, the imaging capsule 100 comprises an encasement 180 shaped as an elongated cylinder with an elongated axis and having flat or spherically shaped ends. Alternatively, other shapes may be used, for example a parallelepiped having flat ends, pyramid shaped ends or other shapes. In an exemplary embodiment of the disclosure, imaging capsule 100 includes a radiation source 110 that emits X-Ray or gamma radiation and is positioned at the center of a collimator 115 (e.g. a circular/cylindrical collimator) to control the direction of emission of radiation from the radiation source 110. Optionally, the radiation source is also located between two radiation blocking disks 125 (e.g. cylindrical tungsten disks) to prevent emission of radiation from the upper and lower ends of the imaging capsule 100.

In an exemplary embodiment of the disclosure, the imaging capsule 100 further includes a power source 150 (e.g. a battery), a controller 130 optionally having a processor and memory and a transceiver 140 for communicating with an external controller or computer 195 to receive instructions and provide measurements/images. In some embodiments of the disclosure, the measurements of the capsule are transmitted to an external recorder and then processed by computer 195 to construct images of the patient's colon based on the measurements. The elements of the imaging capsule 100 (e.g. 120, 130, 140, 150) are connected electronically and/or physically to enable the imaging capsule to function correctly.

In an exemplary embodiment of the disclosure, after swallowing the nanoparticle solution the nanoparticles 170 adhere to cancerous polyps/tumors 160 in the colon 190 of the patient as shown in FIG. 1. Optionally, as imaging capsule 100 traverses the colon it radiates the inner walls of the colon 190 with X-Rays and gamma radiation. In response detectors 120 of imaging capsule 100 detect particles (e.g. photons, electrons) responding to the emitted radiation. Optionally, imaging capsule 100 forms a count for each energy level representing the number of particles having the specific energy level resulting from Compton backscattering and X-Ray fluorescence.

Figure 2:
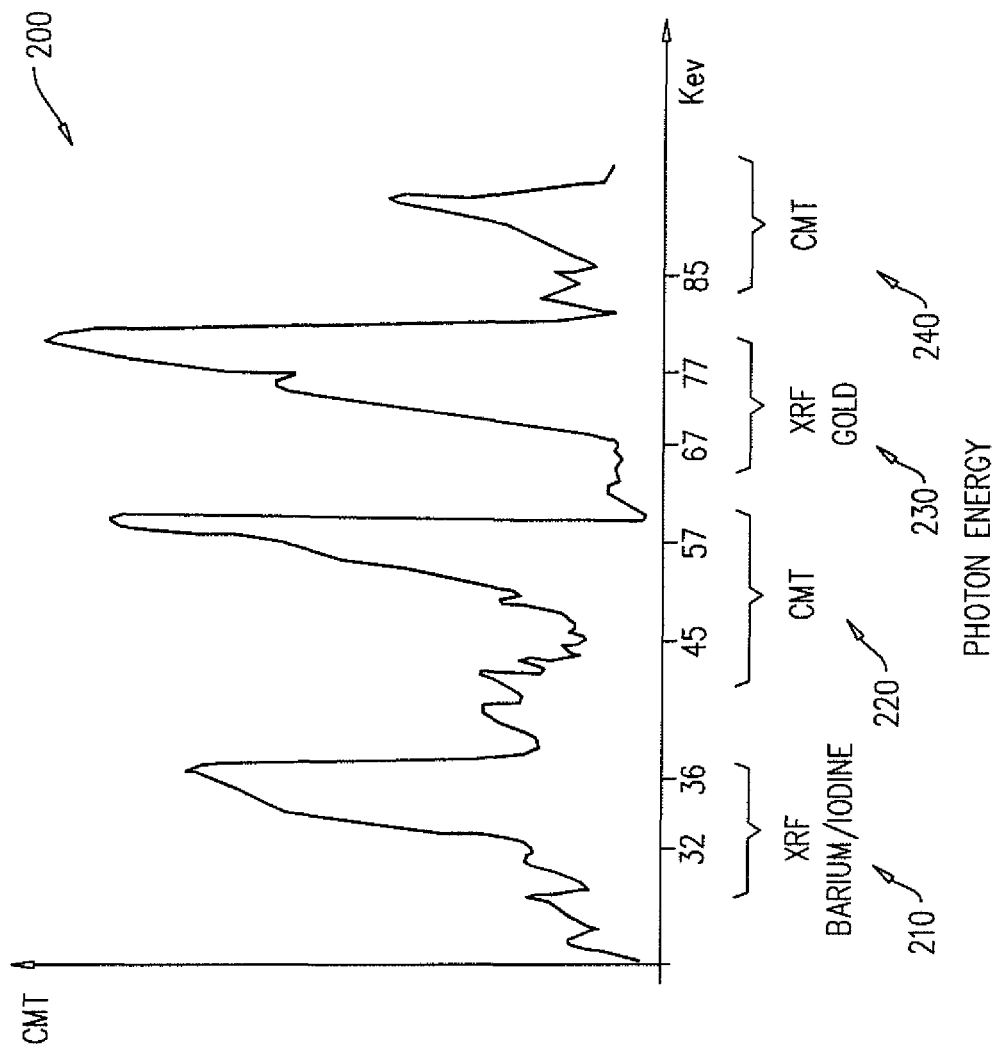
FIG. 2 is a schematic illustration of a graph of a count as a function of the energy of the detected particles, according to an exemplary embodiment of the disclosure.

FIG. 2 is a schematic illustration of a graph 200 of a count as a function of the energy of the detected particles, according to an exemplary embodiment of the disclosure. Optionally, imaging capsule 100 detects three main responses to the radiation source 110:

1. X-Ray fluorescence (210) from the contrast agent (e.g. Barium/Iodine);
2. Compton Backscattering (220) from the contents of the colon 190 surrounding the imaging capsule 110;
3. X-Ray fluorescence (230) from the nanoparticles 170;

In some embodiments of the disclosure a fourth response is detected: Compton Backscattering from the content of the colon at higher energies (240).

In some embodiments of the disclosure, detectors 120 can sample with a high accuracy, for example every one Key or even more accurate (e.g. 0.1 Kev). Alternatively, detectors 120 may be defined with energy windows that count all particles in a specific range (e.g. from 67 Kev to 77 Kev) as a single energy value. Accordingly, the detectors 120 are configured to count particles from 3 or 4 ranges. The detectors then provide a single count value for each range (energy window).

In an exemplary embodiment of the disclosure, the information from the three or four responses is processed by the controller 130 and/or the external controller or computer 195 to construct an image of the colon, for example as illustrated by a snapshot 300 of a computer display in FIG. 3. Optionally, the presence of the nanoparticles 170 coupled to the tumors/polyps and the like along the inner walls of the colon assures that cancerous tissue shines within the colon 190 and is not accidently overlooked, for example computer 195 may show polyps with a special color so that they will stick out for identification by a practitioner. This is especially useful in detecting flat or small cancerous polyps since they don't protrude significantly but the nanoparticles 170 will adhere to them and enhance their visibility to the imaging capsule 100.

In an exemplary embodiment of the disclosure, the radiation source 110 of the capsule 100 needs to provide enough energy to excite the nanoparticles 170 to form X-ray fluorescence. Accordingly, for Gold nanoparticles 170 the capsule X-Ray emissions need to be with an energy higher than the K edge binding energy of the excited atom (in the case of Gold—K edge is at 80.729 Kev).

Optionally, it is preferable to use emissions with the highest possible energies from the X-Ray fluorescence as these have the least attenuation in the body and thus can be sensed at the largest distance. However, it is also possible to detect the lower X-Ray fluorescence energies coming from the L shells (9-13 Kev in the case of Gold (Au79)) If L shell energies are to be detected, the emitted X-Ray radiation from the capsule needs to be higher than the L Edge (14.353 Kev for Gold (Au79)).

Typical x-ray florescence of gold for the K shell is 67, 68 and 77 Kev for Ka1, Ka2 and Kb1 emission lines respectively (see FIG. 2), therefore, in order to detect these X-ray florescence photons, the energy window of the detectors 120 of imaging capsule 100 needs to be set with a low threshold at least below 67 Kev and an upper threshold at least above 77 Kev.

In an exemplary embodiment of the disclosure, Os191 is used as the radiation source 110 for the capsule emitting X-Rays in the energy range of 62-75 Kev and gamma rays with energy of 129 Kev. The x-rays are utilized to excite the radio opaque contrast agent high Z material such as Barium or Iodine which in response emits X-Ray florescence of 32-36 Kev (210) and Compton Backscattering is detected at energies from 49-57 Key (220). It is therefore possible to separate energetically the Compton Backscatter from the X-ray florescence of gold (67-77 Kev (230)) which is excited by the 129 Kev Gamma line of the Os191. Optionally, the 129 Kev line generates 85 Kev backscatter (minimum energy at 180 degrees) so these photons need to be discriminated by setting the upper energy threshold for the gold x-ray florescence at above 77 Kev but below the 85 Kev Compton. Optionally, a fourth energy window (240) may detect Compton Backscattering from the content of the colon at the higher energy.

In some embodiments of the disclosure, Tl201 is used as the radiation source 110 in the imaging capsule 100, in this case the gamma line of 167 Kev from the Tl201 is used to excite the Gold particles. Alternatively or additionally, other radioisotopes or a mixture of radioisotopes are used to produce the measurements.

In some embodiments of the disclosure, the images are constructed based on the X-Ray fluorescence from the contrast agent and the Compton backscattering from the contents of the colon and the colon walls. Optionally, the X-ray fluorescence from the gold nanoparticles 170 is processed separately and is used in forming a correlation between the anatomical (e.g. colon geometry/shape) and physiological elements (e.g. tissue areas that attract the nanoparticles in contrast to tissue areas that do not attract the nanoparticles). Optionally, the X-Ray fluorescence from the nanoparticles serves as an overlay reconstruction layer in the post processing reconstruction to display concentration of detected gold particles over the colon geometry that is reconstructed by computer 195, for example marking the polyp area in the images with specific colors or patterns. In an exemplary embodiment of the disclosure, the count of the gold particles is dependent on the number of nanoparticles 170 that adhere to a specific position in the colon. Optionally, the colors marking the area of a polyp may be brighter or dimmer or of a different shade to provide an indication of the count, which is a function of the number/density of nanoparticles 170 adhering to the area.

Figure 1B:
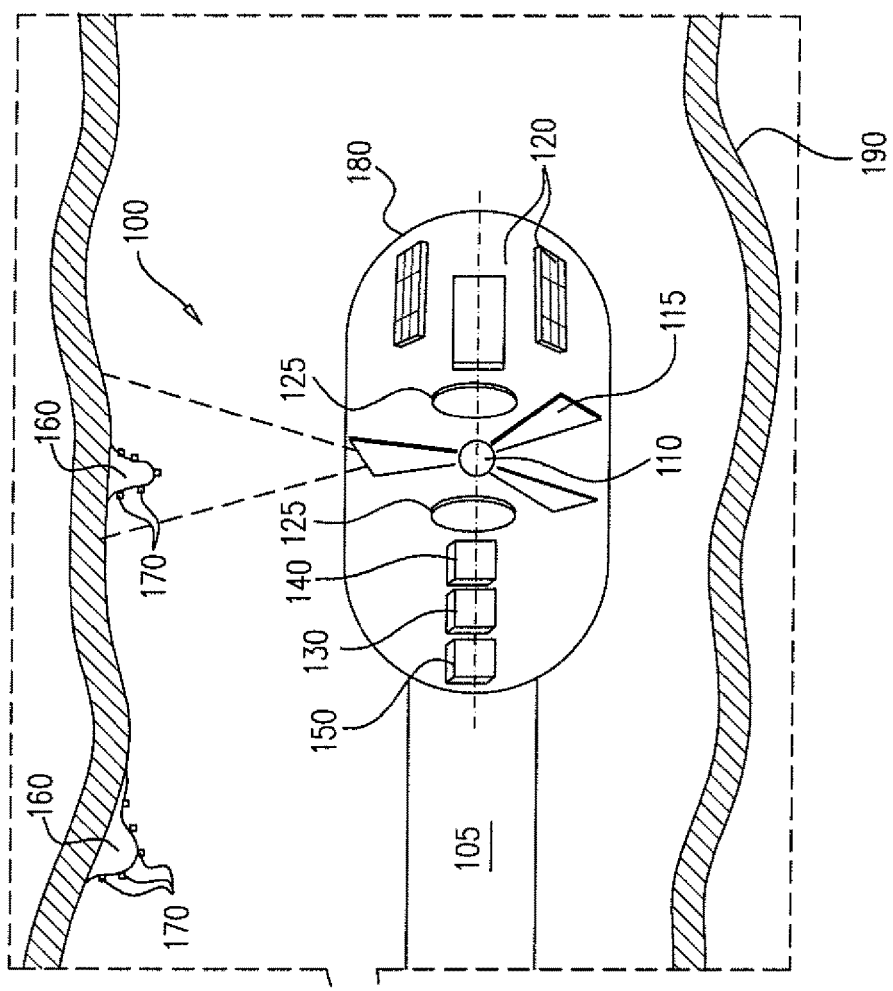
FIG. 1B is a schematic illustration of a perspective view of an imaging capsule in a patient's colon with an insertion tube, according to an exemplary embodiment of the disclosure.
Figure 1B:
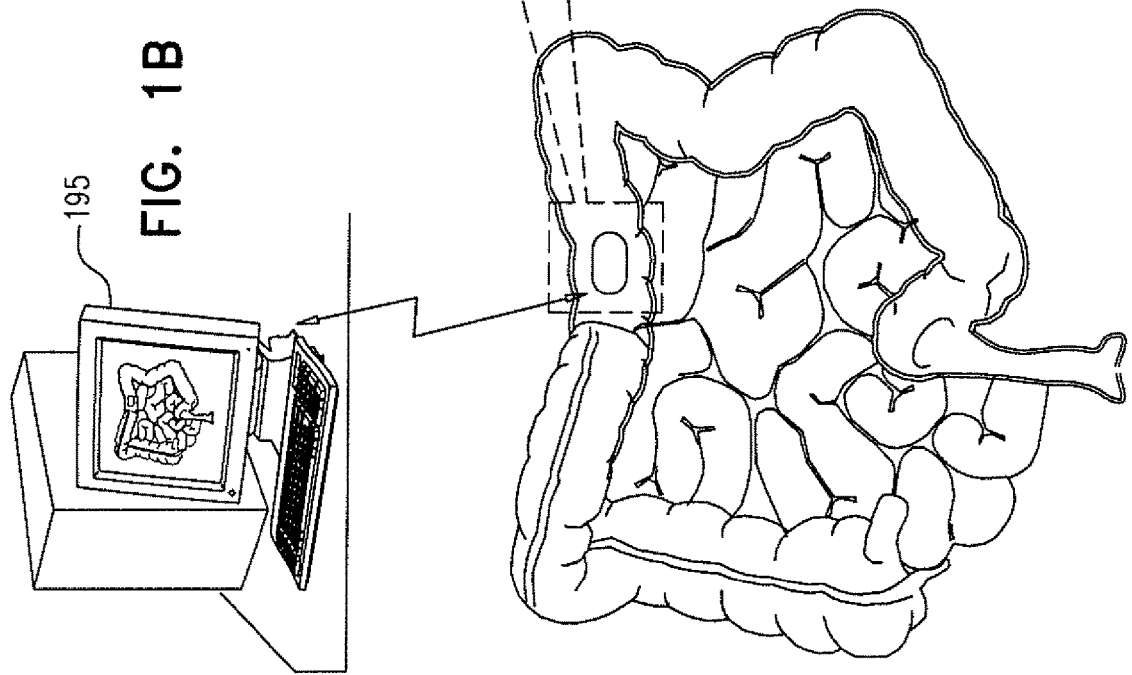

FIG. 1B is a schematic illustration of a perspective view of an imaging capsule 100 in a patient's colon with an insertion tube 105, according to an exemplary embodiment of the disclosure. In some embodiments of the disclosure, imaging capsule 100 may serve as a head for performing a colonoscopy examination instead of being swallowed by the patient. Optionally, imaging capsule 100, emits radiation from radiation source 110 that is capable of exciting the 80 Kev K edge of Gold and/or 14.353 Kev L edge of Gold. The imaging capsule 100 includes radiation detector 120 that is capable of detection of 67, 68 and 77 Kev K shell X-Ray fluorescence of gold and or detection of 9-13 Kev L shell X-Ray fluorescence of Gold. Optionally, the practitioner performing the colonoscopy can see in real time the radiation readings on a display of computer 195. When a high concentration of nanoparticles 170 is detected it signifies that cancerous tissue is located there.

In some embodiments of the disclosure, other materials may be used for the nanoparticles and/or the radiation source 110.

It should be appreciated that the above described methods and apparatus may be varied in many ways, including omitting or adding steps, changing the order of steps and the type of devices used. It should be appreciated that different features may be combined in different ways. In particular, not all the features shown above in a particular embodiment are necessary in every embodiment of the disclosure. Further combinations of the above features are also considered to be within the scope of some embodiments of the disclosure.

It will be appreciated by persons skilled in the art that the present invention is not limited to what has been particularly shown and described hereinabove. Rather the scope of the present invention is defined only by the claims, which follow.

The invention claimed is:

1. A colon imaging system, comprising:
   a) a contrast agent solution, comprising:
      a contrast agent; and
      nanoparticles, which are configured to adhere to cancerous tissue in the colon when swallowed by a patient;
   b) an imaging capsule, comprising:
      a. a radiation source providing X-Ray and gamma radiation with energies sufficient to induce X-Ray fluorescence from the nanoparticles that adhere to cancerous tissue, and which were administered to the patient in the contrast agent solution prior to examining the colon with the imaging capsule;
      b. a detector for detecting particle energy of particles emitted responsive to the provided radiation and forming count information disclosing a number of particles detected for each energy level; wherein the detector includes an energy window configured to detect X-Ray fluorescence from the nanoparticles;
      c. a transceiver for transferring the count information to an external computer for analysis;
   c) a computer for constructing images of an inside of the colon based on the count information; wherein the images provide an indication of locations in the colon of which the nanoparticles adhere to.

2. A colon imaging system according to claim 1, wherein the nanoparticles are made from gold and coated with molecules that adhere to cancerous tissue.

3. A colon imaging system according to claim 1, wherein the imaging capsule is designed to be administered by being swallowed by the patient.

4. A colon imaging system according to claim 1, wherein the imaging capsule is connected to a tube for administering it through the anus of the patient.

5. A colon imaging system according to claim 1, wherein the detector is configured to detect specific ranges of energy levels, forming a single count value for each range and ignoring particles with energies outside of the specific ranges.

6. A colon imaging system according to claim 5, wherein the detected ranges include energy levels representing X-Ray fluorescence resulting from radiating the contents of the colon other than the nanoparticles.

7. A colon imaging system according to claim 5, wherein the detected ranges include energy levels representing X-Ray fluorescence resulting from radiating the nanoparticles.

8. A colon imaging system according to claim 5, wherein the detected ranges include energy levels representing Compton Backscattering resulting from radiating the contents of the colon.

9. A colon imaging system according to claim 5, wherein the detected ranges include energy levels representing Compton Backscattering resulting from particles with energies that are higher than the energies of the X-Ray fluorescence particles.

10. A colon imaging system according to claim 1, wherein the locations of the nanoparticles are marked in the images by specific colors or patterns.

11. A colon imaging system according to claim 1, wherein the markings in the images of the locations of the nanoparticles provide an indication of the density of nanoparticles at the location.

12. A colon imaging system according to claim 1, wherein the image is formed as a combination of the anatomical shape of the colon with the physiological behavior of different tissue areas as an overlay.

13. A method of detecting cancerous tissue in a colon, comprising:
   swallowing a contrast agent solution comprising a contrast agent and nanoparticles that adhere to cancerous tissue in the colon;
   introducing into the colon an imaging capsule to examine the colon;
   radiating internal walls of the colon with a radiation source providing X-Ray and gamma radiation with energies sufficient to induce X-Ray fluorescence from the nanoparticles that adhere to cancerous tissue
   detecting particle energy of particles emitted responsive to the provided radiation and forming count information disclosing a number of particles detected for each energy level; wherein the detector includes an energy window configured to detect X-Ray fluorescence from the nanoparticles;
   transferring the count information to an external computer for analysis;
   constructing images of an inside of a colon based on the count information; wherein the images provide an indication of locations in the colon of which the nanoparticles adhere to.

14. A method according to claim 13, wherein the nanoparticles are made from gold and coated with molecules that adhere to cancerous tissue.

15. A method according to claim 13, wherein the imaging capsule is designed to be administered by being swallowed by the patient.

16. A method according to claim 13, wherein the imaging capsule is connected to a tube for administering it through the anus of the patient.

17. A method according to claim 13, wherein the detector is configured to detect specific ranges of energy levels, forming a single count value for each range and ignoring particles with energies outside of the specific ranges.

18. A method according to claim 17, wherein the detected ranges include energy levels representing X-Ray fluorescence resulting from radiating the nanoparticles.

19. A method according to claim 13, wherein the locations of the nanoparticles are marked in the images by specific colors or patterns.

20. A method according to claim 13, wherein the markings in the images of the locations of the nanoparticles provide an indication of the density of nanoparticles at the location.

* * * * *